(12) United States Patent
Yin

(10) Patent No.: US 11,333,344 B1
(45) Date of Patent: May 17, 2022

(54) MULTIFUNCTIONAL LAMP

(71) Applicant: SHENZHEN COOTWAY TECHNOLOGY CO., LTD., Shenzhen (CN)

(72) Inventor: Benqiang Yin, Shenzhen (CN)

(73) Assignee: SHENZHEN COOTWAY TECHNOLOGY CO., LTD., Shenzhen (CN)

( * ) Notice: Subject to any disclaimer, the term of this patent is extended or adjusted under 35 U.S.C. 154(b) by 0 days.

(21) Appl. No.: 17/246,264

(22) Filed: Apr. 30, 2021

(51) Int. Cl.
  *F21V 31/00* (2006.01)
  *F21V 17/10* (2006.01)
  *A61L 2/02* (2006.01)

(52) U.S. Cl.
  CPC .............. *F21V 31/005* (2013.01); *A61L 2/02* (2013.01); *F21V 17/10* (2013.01)

(58) Field of Classification Search
  CPC ........... F21V 31/005; F21V 17/10; A61L 2/02
  See application file for complete search history.

(56) References Cited

U.S. PATENT DOCUMENTS

| 5,900,212 A * | 5/1999 | Maiden ................... C02F 1/325 |
| | | 422/24 |
| 5,924,784 A * | 7/1999 | Chliwnyj .................. F21V 3/04 |
| | | 362/234 |
| 8,324,595 B2 * | 12/2012 | Takahashi .............. A01K 63/04 |
| | | 250/455.11 |
| 9,346,687 B1 * | 5/2016 | Matthews ............... C02F 1/325 |
| 10,736,978 B2 * | 8/2020 | Reiber .................... C02F 1/325 |
| 2017/0130952 A1 * | 5/2017 | Xu .......................... F21V 23/06 |
| 2020/0041115 A1 * | 2/2020 | Kim ......................... F21V 9/32 |

* cited by examiner

*Primary Examiner* — Arman B Fallahkhair
(74) *Attorney, Agent, or Firm* — Law Offices of Steven W. Weinrieb

(57) ABSTRACT

A multifunctional lamp includes a lighting device and a sterilization device. The lighting device includes a base, a lighting member configured to emit flame-like light; and a light-transmitting suspending chamber defined with a mounting opening. The lighting member is mounted into the light-transmitting suspending chamber through the mounting opening. The light-transmitting suspending chamber is arranged at one side of the base with the base sealing the mounting opening and the sterilization device is arranged at the other side of the base. When the multifunctional lamp is put into liquid, the light-transmitting suspending chamber is capable of floating on the liquid and the sterilization device is capable of being deep into the liquid to sterilize the liquid.

18 Claims, 7 Drawing Sheets

MULTIFUNCTIONAL LAMP

FIELD OF THE INVENTION

The subject matter herein generally relates to lamps, and particularly relates to a multifunctional lamp.

BACKGROUND OF THE INVENTION

With the development of society, people's quality of life is getting higher and higher. In a variety of environmental occasions, different lamps are usually used to provide light. However, with the improvement of people's quality of life, people have more requirements for the functions of lamps. The lamps with only lighting functions cannot meet people's needs. Therefore, a kind of multifunctional lamp is desired.

SUMMARY OF THE INVENTION

The present disclosure provides a multifunctional lamp.

A multifunctional lamp includes a lighting device and a sterilization device. The lighting device includes a base, a lighting member configured to emit flame-like light; and a light-transmitting suspending chamber defined with a mounting opening. The lighting member is mounted into the light-transmitting suspending chamber through the mounting opening and the base is capable of sealing the mounting opening to enable the light-transmitting suspending chamber capable of floating on liquid. The light-transmitting suspending chamber is arranged at one side of the base with the base sealing the mounting opening and the sterilization device is arranged at the other side of the base. When the multifunctional lamp is put into liquid, the light-transmitting suspending chamber is capable of floating on the liquid and the sterilization device is capable of being deep into the liquid to sterilize the liquid.

In at least one embodiment, the light-transmitting suspending chamber includes a first mounting part surrounding the mounting opening, and the base includes a second mounting part corresponding to the first mounting part, the second mounting part is engaged with the first mounting part to mount the light-transmitting suspending chamber onto the base.

In at least one embodiment, a sealing ring is arranged between the light-transmitting suspending chamber and the base and configured to prevent the liquid entering the light-transmitting suspending chamber.

In at least one embodiment, the sterilization device includes a shell defined with a sterilization container configured to contain sterilization substance and a sterilization channel communicating with the sterilization container configured to allow the sterilization substance in contact with the liquid.

In at least one embodiment, the shell is defined with at least one side through hole at a side wall thereof, and/or at least one bottom through hole at a bottom wall thereof, the side through hole or the bottom through hole is communicated with the sterilization channel.

In at least one embodiment, the number of the at least one side through hole is twelve, twelve side through holes are evenly symmetrically arranged at two sides of the shell; and/or the number of the at least one bottom through hole is four, four bottom through holes are evenly arranged at the bottom wall of the shell.

In at least one embodiment, the sterilization container is defined with a first opening, the sterilization device further includes a cover configured to expose or close the first opening.

In at least one embodiment, the shell and the cover are annular, the cover is sleeved on the shell, the cover is defined with a second opening, the cover is capable of rotating relative to the shell between a first position where the first opening is exposed through the second opening and a second position where the second opening is staggered from the first opening and the first opening is closed by an inner wall of the cover.

In at least one embodiment, a size of the second opening is equal to or less than that of the first opening.

In at least one embodiment, the cover is defined with a groove, the shell is provided with a protrude, the protrude is capable of being received in the groove to guide a rotation of the cover relative to the shell.

In at least one embodiment, the base is defined with a slot at the other side of the base, the shell and the cover are partially received in the slot to mount the sterilization device onto the base.

In at least one embodiment, a female thread is provided inside the slot, and a male thread is provided at an outer sidewall of the shell, the male thread is engaged with the female thread to mount the sterilization device onto the base.

In at least one embodiment, the shell includes a first shell part and a second shell part connected with the first shell part and configured to move along an axial direction of the first shell part to change an axial length of the shell.

In at least one embodiment, the first shell part includes a first blocking structure, and the second shell part includes a second blocking structure configured to resist against the first blocking structure to prevent the second shell part moving away from the first blocking part.

In at least one embodiment, the shell includes a third shell part connected with the second shell part and configured to move along an axial direction of the second shell part to change an axial length of the shell.

In at least one embodiment, the second shell part includes a third blocking structure, and the third shell part includes a fourth blocking structure configured to resist against the third blocking structure to prevent the third shell part moving away from the second blocking part.

In at least one embodiment, the lighting device further includes a solar panel and a battery module connected with the solar panel and the lighting member, the solar panel and the battery module are arranged inside the light-transmitting suspending chamber.

In at least one embodiment, the lighting member includes a lighting panel, a mainboard assembly, and a plurality of lighting elements arranged on the lighting panel, the mainboard assembly is configured to control the plurality of lighting elements to emit flame-like light.

In at least one embodiment, the light panel is in a shape of a cylinder, and the plurality of lighting elements are evenly arranged at a peripheral wall of the cylinder.

In at least one embodiment, the lighting member is defined with a receiving cavity for receiving the battery module and the mainboard assembly; the solar panel is arranged at a top wall of the lighting member.

A multifunctional lamp includes a lighting device. The lighting device includes a base; a lighting member configured to emit flame-like light; and a light-transmitting suspending chamber defined with a mounting opening. The lighting member is configured to be mounted into the light-transmitting suspending chamber through the mounting opening and the base is capable of sealing the mounting opening to enable the light-transmitting suspending chamber capable of floating on liquid.

The lighting device of the multifunctional lamp provided by the present disclosure can emit flame-like light. In addition, the light-transmitting suspending chamber can be suspended on the liquid. It is not only useful by providing light but also ornamental. The lighting member can be mounted inside the light-transmitting suspending chamber, and the light-transmitting suspending chamber can be sealed by the base. Therefore, the lighting member is isolated from the liquid, which ensures the light-emitting body work more stably, and the service life of the multifunctional lamp is accordingly improved. Further, the sterilization device can sterilize the liquid, which increase functions of the functional lamp. Both the sterilization device and the lighting member are arranged on the base, which help the user quickly find the sterilization device at night through the light emitted by the lighting member, so that the user can quickly complete replacement and supplement of the sterilization substances in the sterilization device.

BRIEF DESCRIPTION OF THE DRAWINGS

Implementations of the present disclosure will now be described, by way of embodiment, with reference to the attached figures. It should be understood, the drawings are shown for illustrative purpose only, for ordinary person skilled in the art, other drawings obtained from these drawings without paying creative labor by an ordinary person skilled in the art should be within scope of the present disclosure.

DETAILED DESCRIPTION OF THE ILLUSTRATED EMBODIMENTS

Figure 1:
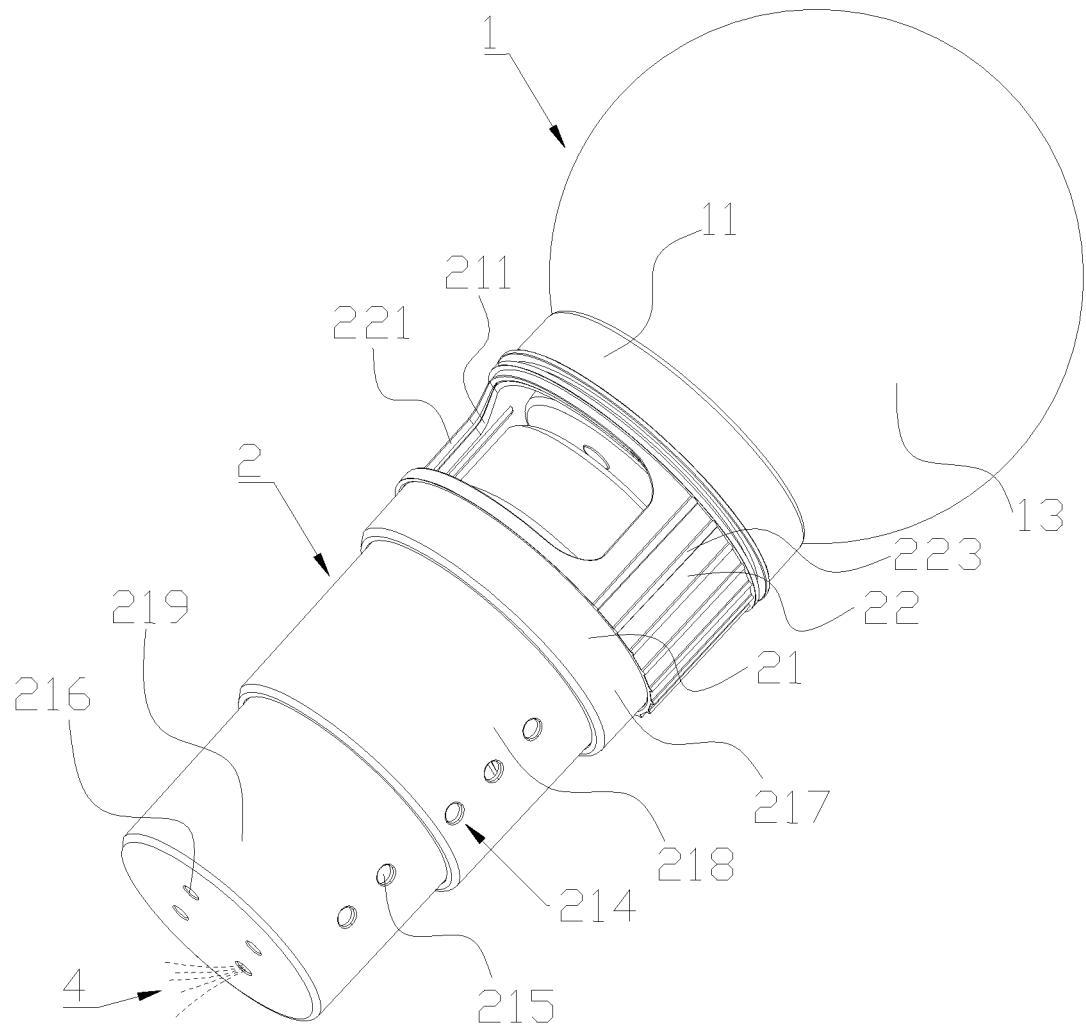
FIG. 1 is a schematic view of a multifunctional lamp with a first opening exposed according to a first embodiment of the present disclosure.

It will be appreciated that for simplicity and clarity of illustration, where appropriate, reference numerals have been repeated among the different figures to indicate corresponding or analogous elements. In addition, numerous specific details are set forth in order to provide a thorough understanding of the exemplary embodiments described herein. However, it will be understood by those of ordinary skill in the art that the exemplary embodiments described herein may be practiced without these specific details. In other instances, methods, procedures, and components have not been described in detail so as not to obscure the related relevant feature being described. Also, the description is not to be considered as limiting the scope of the exemplary embodiments described herein. The drawings are not necessarily to scale and the proportions of certain parts may be exaggerated to better illustrate details and features of the present disclosure.

The term "comprising" when utilized, means "including, but not necessarily limited to"; it specifically indicates open-ended inclusion or membership in the so-described combination, group, series, and the like. The disclosure is illustrated by way of example and not by way of limitation in the figures of the accompanying drawings in which like references indicate similar elements. It should be noted that references to "an" or "one" embodiment in this disclosure are not necessarily to the same embodiment, and such references can mean "at least one". In addition, the terms "first" and "second" are used for descriptive purposes only and cannot be understood as indicating or implying relative importance or implying the number of indicated technical features. Thus, the features defined as "first" and "second" may explicitly or implicitly include one or more of the said features. In the description of embodiments of the invention, "a plurality of" means two or more, unless otherwise specifically defined.

Figure 2:
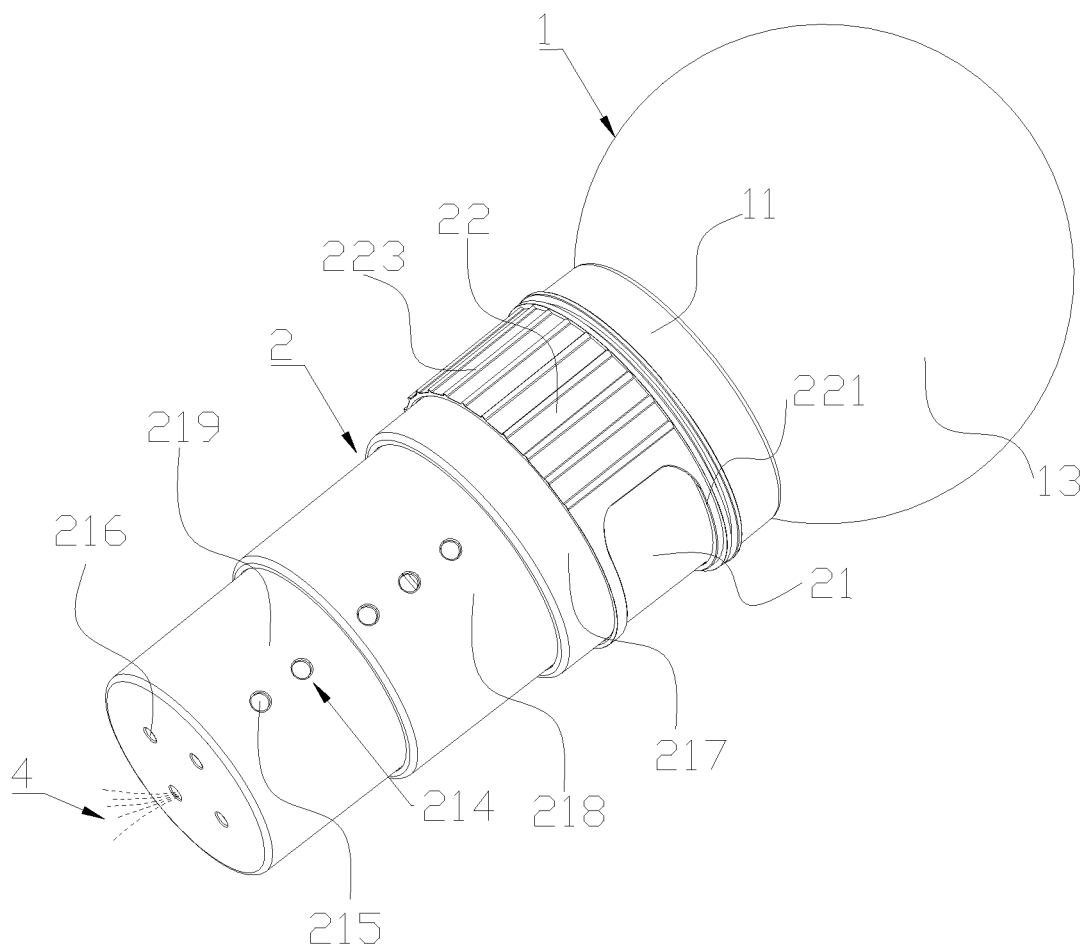
FIG. 2 is schematic view of the multifunctional lamp of FIG. 1 with the first opening closed.

Referring to FIGS. 1-2, a first embodiment of the present disclosure provides a multifunctional lamp including a lighting device 1 and a sterilization device 2. The lighting device 1 includes a base 11, a lighting member 12, and a light-transmitting suspending chamber 13. The lighting member 12 is configured to emit flame-like light. The light-transmitting suspending chamber 13 is defined with a mounting opening 131 through which the lighting member 12 can be mounted inside the light-transmitting chamber 13. The light-transmitting suspending chamber 13 is arranged at an upper side of the base 11 and the sterilization device 2 is arranged at a lower side of the base 11. The base 11 can seal the mounting opening 131. When the multifunction lamp 1 is placed into a container with liquid, the light-transmitting chamber 13 can be suspended on the liquid, and the sterilization device 2 can be deep in the liquid to sterilize the liquid.

The lighting device 1 of the multifunctional lamp provided by the present disclosure can emit flame-like light. In addition, the light-transmitting suspending chamber 13 can be suspended on the liquid. It is not only useful by providing light but also ornamental. The lighting member 12 can be mounted inside the light-transmitting suspending chamber 13, and the light-transmitting suspending chamber 13 can be sealed by the base 11. Therefore, the lighting member 12 is isolated from the liquid, which ensures the light-emitting body work more stably, and the service life of the multifunctional lamp is accordingly improved. Further, the sterilization device 2 can sterilize the liquid, which increase functions of the multifunctional lamp. Both the sterilization device 2 and the lighting member 12 are arranged on the base 11, which help the user quickly find the sterilization device 2 at night through the light emitted by the lighting member 12, so that the user can quickly complete replacement and supplement of the sterilization substances in the sterilization device 2.

In at least one embodiment, the lighting member 12 can be a solar light, which is which is energy-saving and does not need to be connected with a power supply.

In at least one embodiment, the light-transmitting suspending chamber 13 can be a hollow plastic chamber in a shape of sphere. The plastic chamber has long service life, is not easy to break and light weighted. It has good waterproof performance, which can make the multifunctional lamp float on water better.

In at least one embodiment, a sealing ring 111 is arranged between the base 11 and the light-transmitting suspending chamber 13 to prevent the liquid entering the light-transmitting suspending chamber 13, which can further enhance the sealing between the base 11 and the light-transmitting suspending chamber 13. In at least one embodiment, the sealing ring 111 can be made from silica. It can be understood that, in other embodiments, the sealing ring 111 can be made from other elastic materials.

Figure 3:
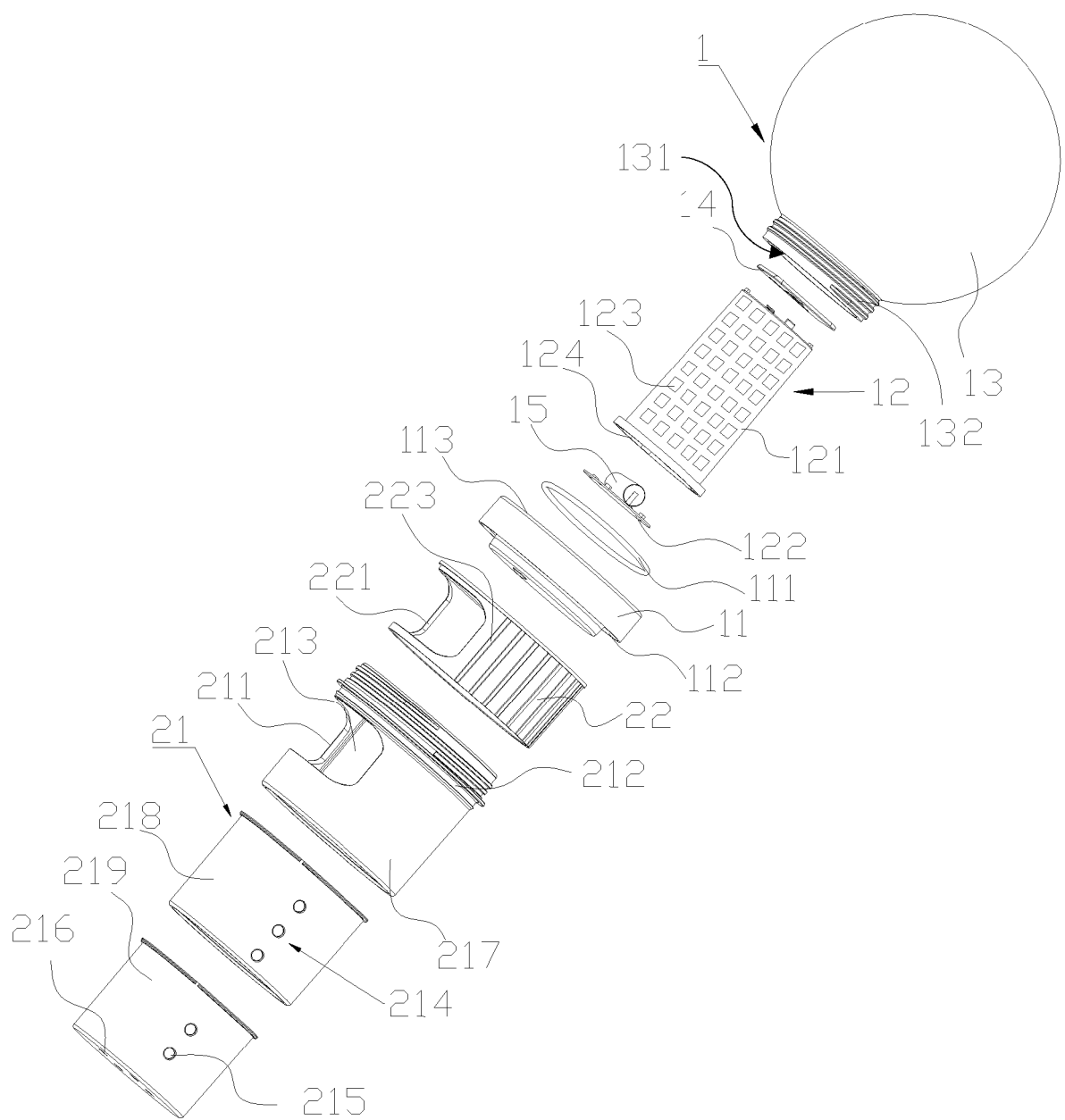
FIG. 3 is an exploded view of the multifunctional lamp of FIG. 1.

In at least one embodiment, referring to FIG. 3, the light-transmitting suspending chamber 13 includes a first mounting part 132, and the base 11 includes a second mounting part 113 corresponding to the first mounting part 132. The first mounting part 132 is formed around the mounting opening 130. In at least one embodiment, the first mounting part 132 is provided with male thread at an inner wall thereof and the second mounting part 113 is provided with female thread at an outer wall thereof. The female thread is engaged with the male thread to connect the base 11 with the light-transmitting suspending chamber 13. In at least one embodiment, the sealing ring 111 resists against the inner wall of the second mounting part 113 and the outer wall of the first mounting part 132. The base 11 can be connected with the light-transmitting suspending chamber 13 through the female thread and the male thread, which is simplified in structure and easy to install. The sealing ring 111 can compensate a gap between the inner wall of the second mounting part 113 and the outer wall of the first mounting part 132, thus improving sealing performance.

It should be understood that, the base 11 can be connected with the light-transmitting suspending chamber 13 with any other suitable structures, such as interference fit, snap fit, and etc.

Figure 4:
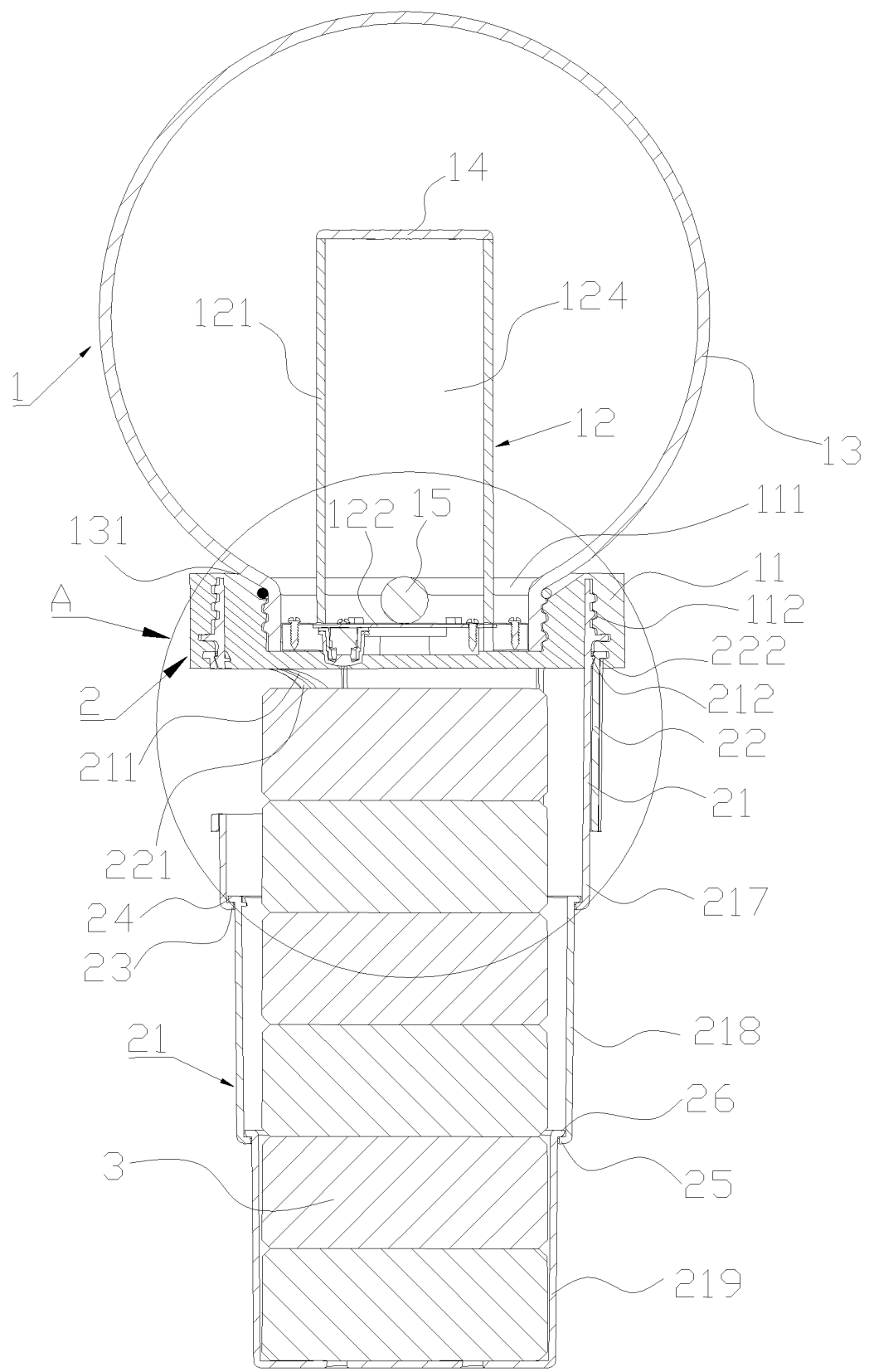
FIG. 4 is a cross-sectional view of the multifunctional lamp of FIG. 1 along the first opening.
Figure 5:
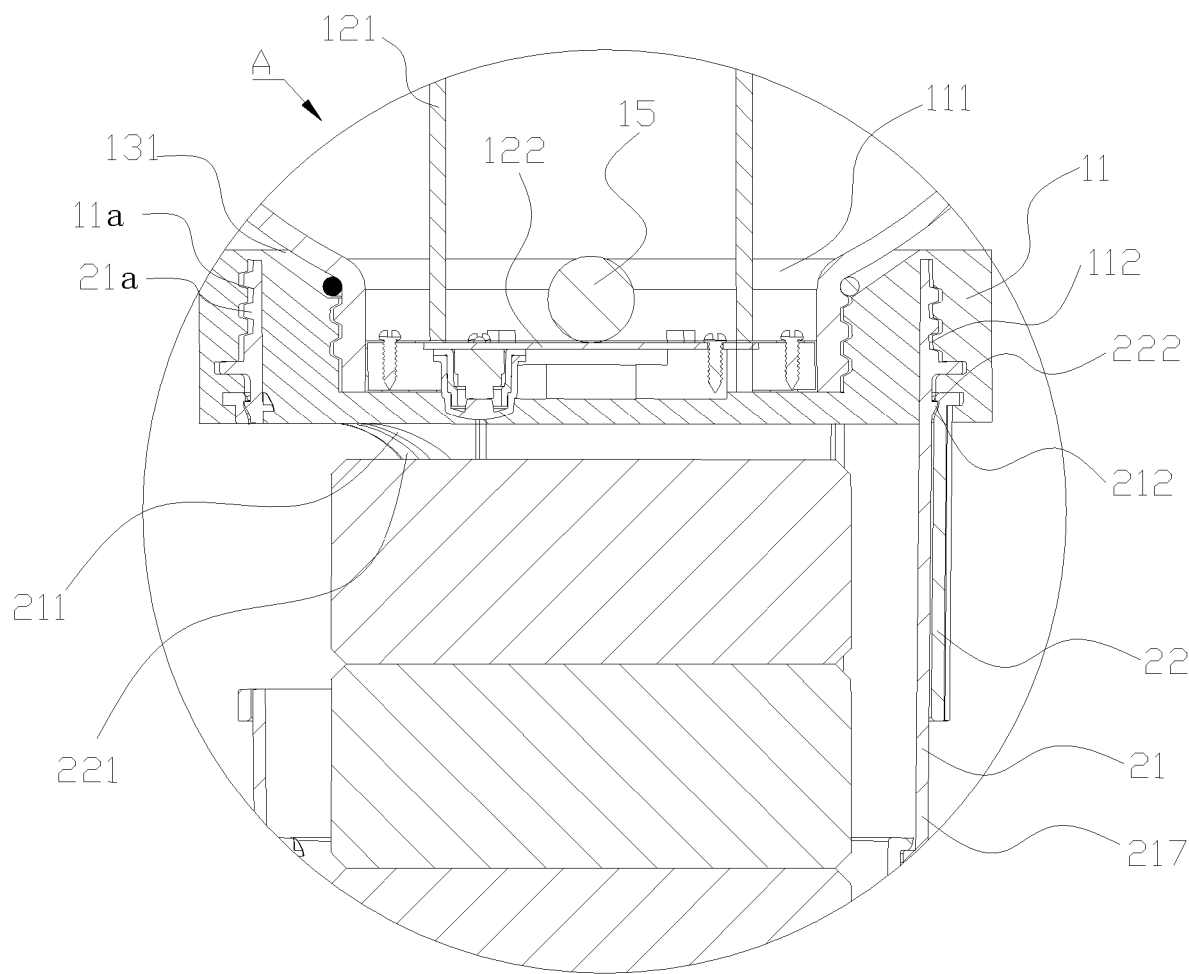
FIG. 5 is an enlarged view of the portion A shown in FIG. 4.
Figure 6:
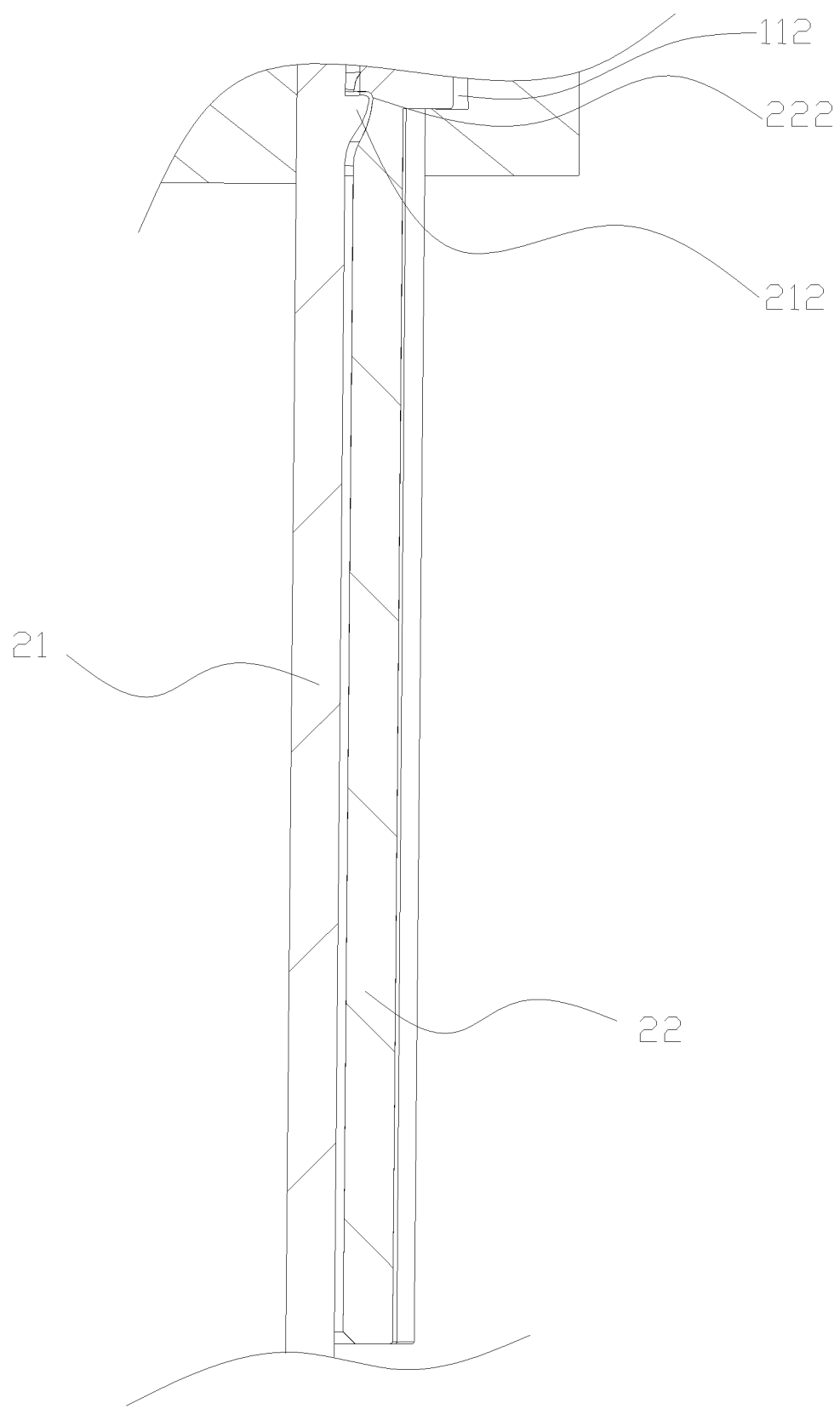
FIG. 6 is a partial cross-sectional view of the multifunctional lamp of FIG. 1.

In at least one embodiment, referring to FIGS. 4-6, the sterilization device 2 includes a shell 21. A sterilization container 213 is arranged inside the shell 21 and a sterilization channel 214 communicating with the sterilization container 213. The sterilization container 213 is configured to contain sterilization substance, such as chlorine. The sterilization channel 214 is configured to communicate the sterilization container 213 with an outside of the case 21, therefore, the sterilization substance contained inside the sterilization container 213 can contact the liquid outside the shell 21.

In at least one embodiment, at least one side through hole 215 is defined at a side wall of the shell 21 communicating with the sterilization channel 214. In at least one embodiment, at least one bottom through hole 216 is defined at a bottom wall of the shell 21 communicating with the sterilization channel 214. In at least one embodiment, the number of the at least one side through hole 215 is twelve. Twelve side through holes 215 are arranged in two columns which vertically symmetrically on the side wall of the shell 21. The number of the at least one bottom through hole 216 is four. Four bottom through holes 216 are arranged evenly and symmetrically on the bottom wall of the shell 21. The sterilization substance contained in the sterilization container 213 can be distributed into the liquid through the at least one side through hole 215 and the at least one bottom through hole 216 to sterilize the liquid.

In at least one embodiment, the sterilization container 213 is defined with a first opening 211 configured to allow a user to add sterilization substance into the sterilization container 213 therethrough. The sterilization device 2 can includes a cover 22 configured to cover or close the first opening 211.

In at least one embodiment, the shell 21 is circular, the cover 22 is circular and sleeved on the shell 21. The cover 22 is defined with a second opening 221. The cover 22 can rotate relative to the shell 21 between a first position where the second opening 221 is corresponding to the first opening 211 to expose the first opening 211 and a second position where the second opening 221 is staggered from the first opening 211 to close the first opening 211 with an inner wall of the cover 22.

The first opening 211 can be closed by the inner wall of the cover 22, thus protecting the sterilization substance contained in the sterilization container 213 from being spilled out. The first opening 211 can be easily exposed by rotating the cover 22 relative to the shell 21 to facilitate adding or replacing sterilization substance into the sterilization container 213. The structure is simplified and easy to operate, thus improving user's experience.

In at least one embodiment, a size of the second opening 221 is greater than that of the first opening 211, therefore, when the cover 22 is rotated to the first position, the first opening 211 can be wholly exposed through the second opening 221. In this way, sterilization substance can be easily added or replaced through the first opening 211.

In at least one embodiment, a plurality of anti-slip structure 223 is formed at an outer wall of the cover 22. The anti-slip structure 223 can increase fiction between user's finger and the cover 22, which can help a user easily rotates the cover 22 relative to the shell 21.

In at least one embodiment, a groove 222 is defined around an inner wall of the cover 22, and a protrude 212 corresponding to the groove 222 extends from an outer wall of the shell 21. The protrude 212 is received in the groove 222 to guide rotation of the cover 22 relative to the shell 21.

In at least one embodiment, the groove 222 and the protrude 212 are triangle. The protrude 212 includes a first surface and a second surface. A third surface together with a fourth surface define the groove 222. The first surface resists against the third surface, and the second surface resists against the fourth surface, which can make the connection between the cover 22 and the shell 21 close, and can effectively prevent shaking of the cover 22 relative to the shell 21.

In at least one embodiment, the base 11 is defined with a slot 112 at the lower side thereof. A side wall of the shell 21 together with a side wall of the cover 22 can be received in the slot 112, so that the sterilization device 2 is mounted onto the base 11. The structure for mounting the sterilization device 2 onto the base 11 is simple and stable.

In at least one embodiment, a female thread 11a is provided inside the slot 112, and a male thread 21a is provided at the side wall of the shell 21 and the cover 22 facing the slot 112. The male thread 21a is engaged with the female thread 11a to mount the sterilization device 2 onto the base 11.

In at least one embodiment, the shell 21 can include a first shell part 217, a second shell part 218 connected with the first shell part 217, and a third shell part 219 connected with the second shell part 218. The first shell part 217 is sleeved on the second shell part 218 and can move along an axis direction of the first shell part 217 relative to the first shell part 217 so as to change an axial length of the shell 21. The first shell part 217 forms a first blocking structure 23, and the second shell part 217 forms a second blocking structure 24. The first blocking structure 23 can resist against the second blocking structure 24 to prevent the second shell part 218 from moving away from the first shell part 217. In at least one embodiment, the first blocking structure 23 is arranged at an end of the first shell part 217 away from the base 11, the second blocking structure 24 is arranged at an end of the second shell part 218 near the base 11. Similarly, the second shell part 218 is sleeved on the third shell part 219 and can move along an axis direction of the second shell part 218 relative to the second shell part 218 so as to further change the axial length of the shell 21. The second shell part 218 forms a third blocking structure 25, and the third shell part 219 forms a fourth blocking structure 26. The third blocking structure 25 can resist against the fourth blocking structure 26 to prevent the third shell part 219 from moving away from the second shell part 218. In at least one embodiment, the third blocking structure 25 is arranged at an end of the second shell part 218 away from the base 11, and the fourth blocking structure 26 is arranged at an end of the third shell part 219 near the base 11. In this way, the axial length of the shell 21 can be increased, therefore, the shell 21 can contain more sterilization substance.

The axial length of the shell 21 can be easily changed by moving the second shell part 218 and the third shell part 219 relative to the first shell part 217. The first blocking structure 23 and the second blocking structure 24 can prevent the second shell part 218 from moving away the first shell part 218, the third blocking structure 25 and the fourth blocking structure 26 can prevent the third shell part 219 from moving away the second shell part 218, which keeps the first shell part 217, the second shell part 218, and the third shell part 219 always connected together.

In at least one embodiment, the first shell part 217, the second shell part 218 and the third shell part 219 are hollow cylinder, which make the moving of the second shell part 218 and the third shell part 219 more smoothly.

In at least one embodiment, a diameter of the second shell part 218 is equal to or less than that of the first shell part 217, a diameter of the third shell part 219 is equal to or less than that of the second shell part 218. An axial length of the second shell part 218 is equal to or less than that of the first shell part 217, and an axial length of the third shell part 219 is equal to or less than that of the second shell part 218. Therefore, the third shell part 219 can be totally received inside the second shell part 218, and the second shell part 218 can be totally received inside the first shell part 217. Thus, the sterilization device 2 can be put in the liquid with different heights.

In at least one embodiment, the multifunctional lamp 1 further includes a solar panel 14 and a battery module 15. Both the solar panel 14 and the battery module 15 are arranged inside the light-transmitting suspending chamber 13. The battery module 15 is connected between the solar panel 14 and the lighting member 12. The solar panel 14 collects energy from sun and the energy is used to charge the battery module 15. The battery module 15 is configured to supply power to the lighting member 12 so that the lighting member 12 can emit light. The lighting member 12 includes a lighting body 121, a mainboard assembly 122 and a plurality of lighting elements 123 like LEDs. The lighting body 121 is in a shape of a cylinder. The plurality of lighting elements 123 is evenly arranged at a peripheral wall of the cylinder. The mainboard assembly 122 is connected with the plurality of lighting elements 123 and configured to control the lighting elements 123 to emit light in a shape like flame.

The solar panel 14 can collect energy from sun, which is energy saving. The battery module 15 can store energy and supply energy to the lighting member 12, which ensure the lighting member 12 can emit light even at night or other overcast or foggy weather. The battery module 15 supplies power to the lighting member 12 can make the lighting member 12 free of connecting to external power supply, which is convenient for use in any environment.

In at least one embodiment, the lighting member 12 is defined with a receiving cavity 124 for receiving the battery module 15 and the mainboard assembly 122, which make the lighting member 12 is simple and compact in structure.

The solar panel 14 can be arranged at a top wall of the lighting member 12, which facilitate collecting energy of the solar panel 14 from the sun, thus improving efficiency of the solar panel 14.

Figure 7:
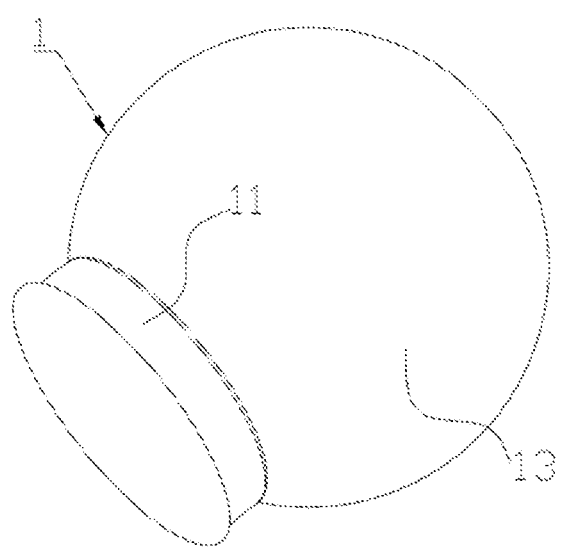
FIG. 7 is a schematic view of a multifunctional lamp according to a second embodiment of the present disclosure.

Referring to FIG. 7, a second embodiment of the present disclosure provides a multifunctional lamp. In the second embodiment, the multifunctional lamp includes the lighting device 1 and the sterilization device 2 is removed. The lighting device 1 has been described in detail in the above embodiments. The base 11 seals the light-transmitting suspending chamber 13 to form a sealed receiving space where the lighting member 12 is arranged. Therefore, the multifunctional lamp can make the light-transmitting suspending chamber 13 float on the liquid while the lighting member 12 is Protected from being damaged due to the liquid. The light emitted from the lighting member 12 can be transmitted through the light-transmitting suspending chamber 13 to provide light. The multifunction lamp of the second embodiment has advantages of novel appearance, strong decorativeness, simple structure, convenience and practicability.

The above description only describes embodiments of the present disclosure, and is not intended to limit the present disclosure, various modifications and changes can be made to the present disclosure. Any modifications, equivalent substitutions, improvements, or the like, made within the spirit and scope of the present disclosure are intended to be included within the scope of the present disclosure.

What is claimed is:

1. A multifunctional lamp, comprising:
a base;
a lighting member configured to emit a flame-like light;
a light-transmitting suspending chamber defined with a mounting opening, wherein said lighting member is configured to be mounted within said light-transmitting suspending chamber through said mounting opening; and said base is capable of sealing said mounting opening;
a sterilization device, wherein said light-transmitting suspending chamber is arranged upon one side of said base and said sterilization device is arranged upon the other side of said base, such that when said multifunctional lamp is put into liquid, said light-transmitting suspending chamber is capable of floating upon the liquid and said sterilization device is capable of being immersed within said liquid so as to sterilize the liquid; and
wherein said sterilization device comprises a shell defined with a sterilization container configured to contain a sterilization substance and a sterilization channel communicating with said sterilization container configured to allow the sterilization substance to be in contact with the liquid.

2. The multifunctional lamp according to claim 1, wherein the sterilization container is defined with a first opening, the sterilization device further includes a cover configured to expose or close the first opening.

3. The multifunctional lamp according to claim 2, wherein the base is defined with a slot at the other side of the base, the shell and the cover is partially received in the slot to mount the sterilization device onto the base.

4. The multifunctional lamp according to claim 3, wherein a female thread is provided inside the slot, and a male thread is provided at an outer sidewall of the shell, the male thread is engaged with the female thread to mount the sterilization device onto the base.

5. The multifunctional lamp according to claim 2, wherein the shell and the cover are annular, the cover is sleeved on the shell, the cover is defined with a second opening, the cover is capable of rotating relative to the shell between a first position where the first opening is exposed through the second opening and a second position where the second opening is staggered from the first opening and the first opening is closed by an inner wall of the cover.

6. The multifunctional lamp according to claim 2, wherein a size of the second opening is equal to or less than that of the first opening.

7. The multifunctional lamp according to claim 2, wherein the cover is defined with a groove, the shell is provided with a protrude, the protrude is capable of being received in the groove to guide a rotation of the cover relative to the shell.

8. The multifunctional lamp according to claim 1, wherein the shell comprises a first shell part and a second shell part connected with the first shell part and configured to move along an axial direction of the first shell part to change an axial length of the shell.

9. The multifunctional lamp according to claim 8, wherein the shell comprises a third shell part connected with the second shell part and configured to move along an axial direction of the second shell part to change an axial length of the shell.

10. The multifunctional lamp according to claim 9, wherein the second shell part comprises a third blocking structure, and the third shell part comprises a fourth blocking structure configured to resist against the third blocking structure to prevent the third shell part moving away from the second blocking part.

11. The multifunctional lamp according to claim 8, wherein the first shell part comprises a first blocking structure, and the second shell part comprises a second blocking structure configured to resist against the first blocking structure to prevent the second shell part moving away from the first blocking part.

12. The multifunctional lamp according to claim 1, wherein a sealing ring is arranged between the light-transmitting suspending chamber and the base and configured to prevent the liquid entering the light-transmitting suspending chamber.

13. The multifunctional lamp according to claim 1, wherein the lighting device further comprises a solar panel and a battery module connected with the solar panel and the lighting member, the solar panel and the battery module are arranged inside the light-transmitting suspending chamber.

14. The multifunctional lamp according to claim 1, wherein the lighting member comprises a lighting panel, a mainboard assembly, and a plurality of lighting elements arranged on the lighting panel, the mainboard assembly is configured to control the plurality of lighting elements to emit flame-like light.

15. The multifunctional lamp according to claim 1, wherein the light panel is in a shape of a cylinder, and the plurality of lighting elements are evenly arranged at a peripheral wall of the cylinder.

16. The multifunctional lamp according to claim 1, wherein the lighting member is defined with a receiving cavity for receiving the battery module and the mainboard assembly; the solar panel is arranged at a top wall of the lighting member.

17. A multifunctional lamp comprising: a base; a lighting member configured to emit flame-like light; and a light-transmitting suspending chamber defined with a mounting opening, wherein the lighting member is configured to be mounted into the light-transmitting suspending chamber through the mounting opening and the base is capable of sealing the mounting opening to enable the light-transmitting suspending chamber capable of floating on a liquid; a sterilization device arranged upon an other side of said base from the light-transmitting suspending chamber and comprising a shell defined within a sterilization container configured to contain a sterilization substance and a sterilization channel communicating with said sterilization container configured to allow the sterilization substance to be in contact with the liquid; and wherein said shell is defined with at least one side through hole in a side wall thereof, and at least one bottom through hole in a bottom wall thereof, and wherein at least one of said side through hole and said bottom through hole is in communication with said sterilization channel.

18. The multifunctional lamp according to claim 17, wherein the number of the at least one side through hole is twelve, twelve side through holes are evenly symmetrically arranged at two sides of the shell; and/or the number of the at least one bottom through hole is four, four bottom through holes are evenly arranged at the bottom wall of the shell.

\* \* \* \* \*